(12) United States Patent
Jolly et al.

(10) Patent No.: US 9,138,223 B2
(45) Date of Patent: Sep. 22, 2015

(54) DRILL PIN FOR SUTURE PASSING

(75) Inventors: Jacob A. Jolly, Naples, FL (US); Robert T. Burks, Salt Lake City, UT (US)

(73) Assignee: Arthrex, Inc., Naples, FL (US)

( * ) Notice: Subject to any disclaimer, the term of this patent is extended or adjusted under 35 U.S.C. 154(b) by 788 days.

(21) Appl. No.: 12/709,314

(22) Filed: Feb. 19, 2010

(65) Prior Publication Data

US 2010/0217315 A1 Aug. 26, 2010

Related U.S. Application Data

(60) Provisional application No. 61/153,822, filed on Feb. 19, 2009.

(51) Int. Cl.
| | |
|---|---|
| A61F 2/08 | (2006.01) |
| A61B 17/06 | (2006.01) |
| A61B 17/00 | (2006.01) |
| A61B 17/16 | (2006.01) |
| A61B 17/88 | (2006.01) |
| A61B 17/04 | (2006.01) |

(52) U.S. Cl.
CPC .............. *A61B 17/06* (2013.01); *A61B 17/1697* (2013.01); *A61B 17/8897* (2013.01); *A61F 2/0805* (2013.01); *A61B 17/0482* (2013.01); *A61F 2/0811* (2013.01); *A61F 2002/0852* (2013.01); *A61F 2230/0086* (2013.01); *A61F 2310/00017* (2013.01)

(58) Field of Classification Search
CPC ................ A61F 2/0811; A61F 2/0805; A61F 2002/0852; A61F 2230/0086; A61F 2002/0876; A61F 2002/0882; A61F 2002/0888; A61B 17/8897; A61B 17/06; A61B 17/1697; A61B 17/0482; A61B 17/1764; A61B 17/1675; A61B 17/16; A61B 17/1615; A61B 17/1617
USPC .................. 623/13.11–13.2; 606/80, 222–227
See application file for complete search history.

(56) References Cited

U.S. PATENT DOCUMENTS

| | | | |
|---|---|---|---|
| 4,182,341 A * | 1/1980 | Perri | 606/225 |
| 5,211,647 A | 5/1993 | Schmieding | |
| 5,306,301 A | 4/1994 | Graf et al. | |
| 5,320,115 A | 6/1994 | Kenna | |
| 5,320,626 A | 6/1994 | Schmieding | |
| 5,370,662 A | 12/1994 | Stone et al. | |
| 5,549,613 A | 8/1996 | Goble et al. | |

(Continued)

FOREIGN PATENT DOCUMENTS

| | | |
|---|---|---|
| EP | 0 495 487 A2 | 7/1992 |
| EP | 0 556 570 A1 | 8/1993 |
| EP | 1884200 A2 * | 2/2008 |

*Primary Examiner* — Andrew Iwamaye
(74) *Attorney, Agent, or Firm* — Dickstein Shapiro LLP

(57) ABSTRACT

A method and apparatus for anatomical tissue repair, such as ligament repair and reconstruction with suture and/or graft passage, employing a pin with a suture passing mechanism. The suture passing mechanism may include a loop (for example, a wire loop or suture loop) securely attached to a pin (for example, a drill pin). The loop may be crimped onto the pin, or welded on the end of the drill pin (in place of the eyelet formed within the pin), to alleviate the difficulty in threading the eyelet and to lower the manufacturing cost of the pin. The suture passing mechanism may alternatively include a slotted suture eyelet (i.e., a longitudinal slot) provided at a proximal end of a pin, to allow suture loading from the side of the instrument.

2 Claims, 8 Drawing Sheets

(56) References Cited

U.S. PATENT DOCUMENTS

| | | | |
|---|---|---|---|
| 5,603,716 A * | 2/1997 | Morgan et al. | 606/88 |
| 5,645,588 A | 7/1997 | Graf et al. | |
| 5,713,905 A * | 2/1998 | Goble et al. | 606/80 |
| 6,132,433 A * | 10/2000 | Whelan | 606/916 |
| 6,235,057 B1 | 5/2001 | Roger et al. | |
| 6,306,138 B1 | 10/2001 | Clark et al. | |
| 6,419,700 B2 * | 7/2002 | Huene | 623/13.14 |
| 6,562,071 B2 * | 5/2003 | Jarvinen | 623/13.14 |
| 6,599,289 B1 | 7/2003 | Bojarski et al. | |
| 6,623,524 B2 * | 9/2003 | Schmieding | 623/13.14 |
| 6,641,395 B2 | 11/2003 | Kumar et al. | |
| 6,716,234 B2 | 4/2004 | Grafton et al. | |
| 6,886,569 B2 | 5/2005 | Chervitz et al. | |
| 7,637,910 B2 * | 12/2009 | Schmieding et al. | 606/80 |
| 8,038,678 B2 * | 10/2011 | Schmieding et al. | 606/80 |
| 2002/0007182 A1 * | 1/2002 | Kim | 606/53 |
| 2002/0040241 A1 * | 4/2002 | Jarvinen | 623/13.14 |
| 2002/0055749 A1 * | 5/2002 | Esnouf et al. | 606/148 |
| 2002/0188298 A1 * | 12/2002 | Chan | 606/72 |
| 2003/0050666 A1 | 3/2003 | Grafton | |
| 2003/0065391 A1 | 4/2003 | Re et al. | |
| 2003/0167090 A1 * | 9/2003 | Chervitz et al. | 623/13.14 |
| 2004/0199166 A1 | 10/2004 | Schmieding et al. | |
| 2005/0261766 A1 * | 11/2005 | Chervitz et al. | 623/13.14 |
| 2007/0162125 A1 * | 7/2007 | LeBeau et al. | 623/13.14 |
| 2008/0188935 A1 | 8/2008 | Saylor et al. | |

* cited by examiner

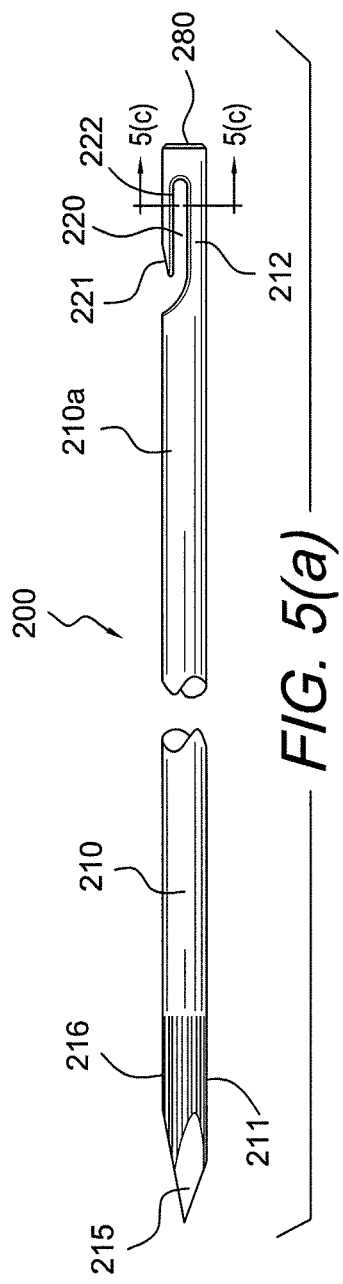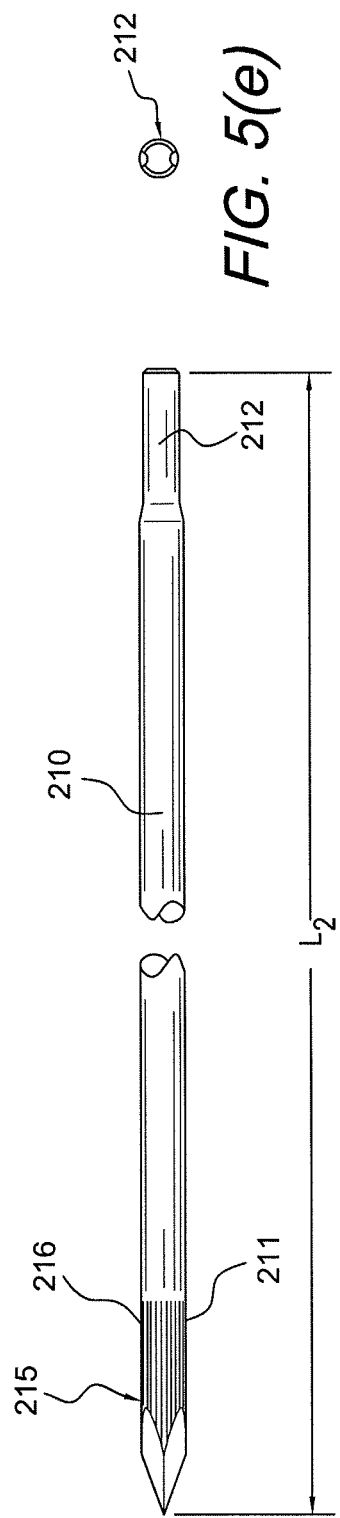

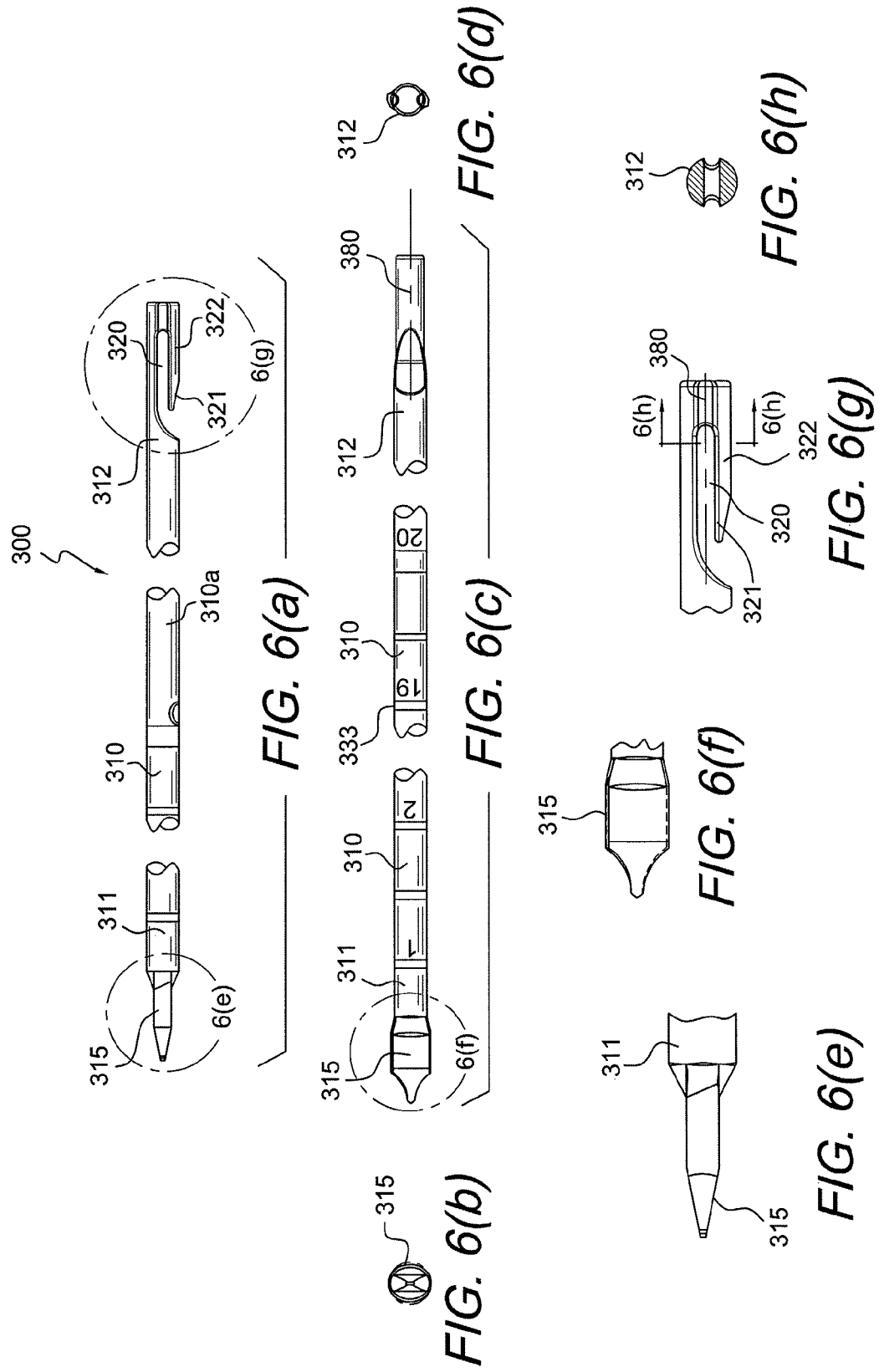

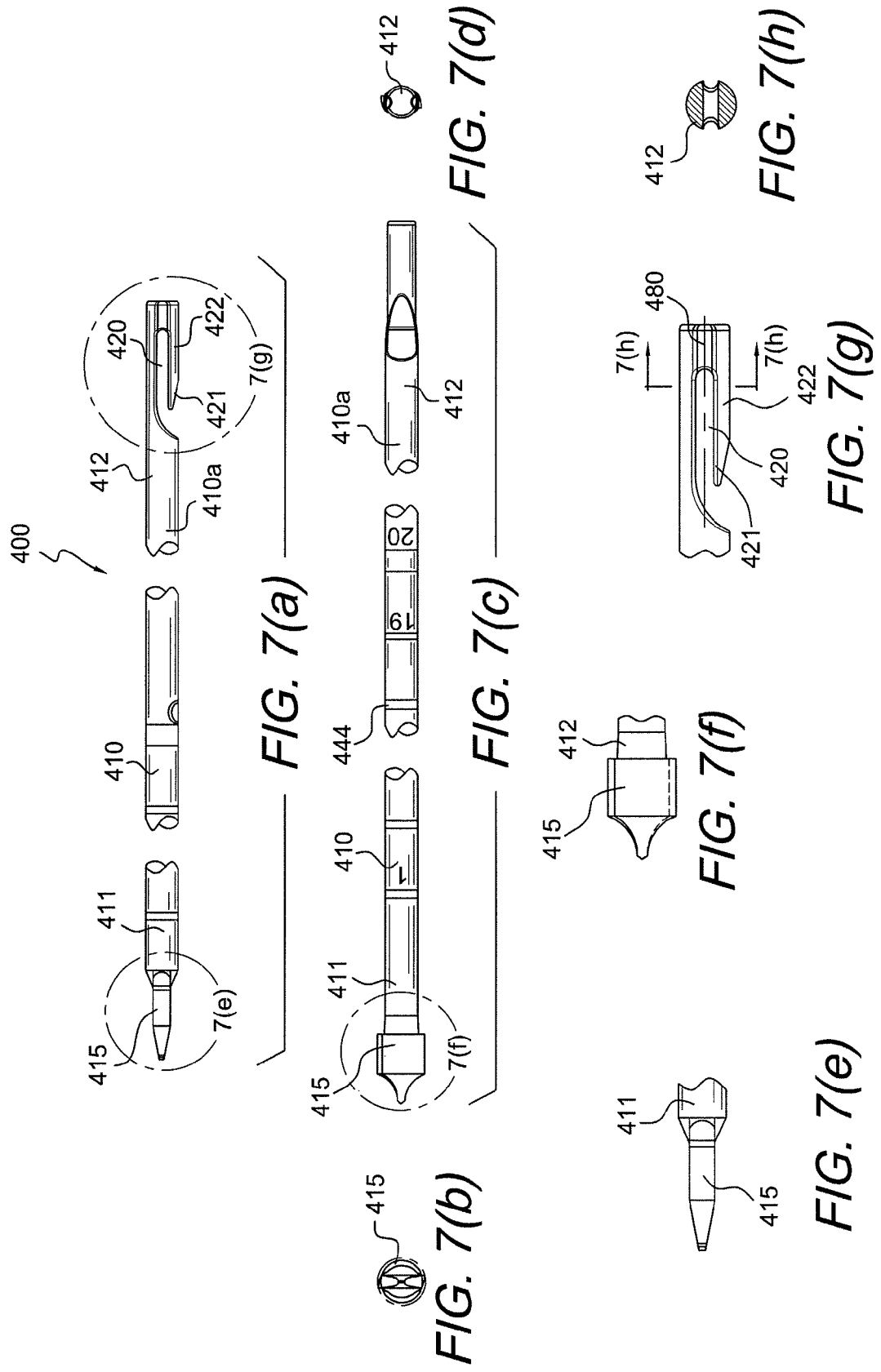

DRILL PIN FOR SUTURE PASSING

CROSS-REFERENCE TO RELATED APPLICATIONS

This application claims the benefit of U.S. Provisional Application No. 61/153,822, filed Feb. 19, 2009, the entire disclosure of which is incorporated by reference herein.

FIELD OF THE INVENTION

The present invention relates to instruments and methods of surgery using a drill pin for suture passing in connection with the treatment tissue.

BACKGROUND OF THE INVENTION

When a ligament or tendon becomes detached from the bone, surgery is usually required to re-secure the ligament or tendon. Often, a substitute ligament or graft is attached to the bone to facilitate regrowth and permanent attachment. The reattachment procedure involves drilling of a graft tunnel between two bones (for example, femur and tibia) and then securing of the tissue (graft) within the tunnel.

Ordinarily, an incision is made to access the proper area for drilling a tunnel through the bone. A guide pin is placed through the incision and driven into the bone. A drill is then placed over and guided by the guide pin during the drilling of the graft tunnel through the bone.

Currently, certain drill pins, guide pins and/or beath pins are provided with small suture eyelets in the shaft for threading and passing sutures or flexible strands. For example, FIG. 1 illustrates a known suture pin 10 provided with a 2.4 mm suture eyelet 11. However, it remains difficult to thread the sutures or strands with the attached graft through (particularly when multiple strands are employed). The procedure is also time consuming and difficult, as it requires loading of multiple suture strands through the small eyelets in the pins. In addition, manufacturing of drill pins, guide pins and/or beath pins with small suture eyelets in the shaft is costly.

Improved suture/pin constructs and methods of threading suture through tissue, or around tissue, with maximum suture fixation strength, as well as methods of securing tissue to tissue are needed.

SUMMARY OF THE INVENTION

The present invention provides instruments and methods for anatomical tissue repair, such as ligament repair and reconstruction with suture and/or graft passage, employing a pin with a suture passing mechanism. The suture passing mechanism may include a loop (for example, a wire loop or suture loop) securely attached to the pin (for example, a drill pin). The loop may be crimped onto the pin, or welded on the end of the drill pin (in place of the eyelet formed within the pin), to alleviate the difficulty in threading the eyelet and to lower the manufacturing cost of the pin.

Alternatively, the suture passing mechanism may include a slotted suture eyelet (i.e., a longitudinal slot) provided at a proximal end of the pin, to allow suture loading from the side of the instrument. In this manner, loading of the sutures on the pin becomes less difficult and the overall procedure is less time consuming.

These and other features and advantages of the invention will be more apparent from the following detailed description that is provided in connection with the accompanying drawing and illustrated exemplary embodiments of the invention.

BRIEF DESCRIPTION OF THE DRAWINGS

FIG. 5(a) illustrates a front view of a suture pin (2.4 mm pin) with a slotted open eyelet, and in accordance with a second embodiment of the present invention;

FIG. 5(b) illustrates a left side view of the suture pin of FIG. 5(a);

FIG. 5(c) illustrates a cross-sectional view of the suture pin of FIG. 5(a), taken along line A-A of FIG. 5(a);

FIG. 5(d) illustrates atop view of the suture pin of FIG. 5(a);

FIG. 5(e) illustrates a right side view of the suture pin of FIG. 5(d);

FIG. 6(a) illustrates a front view of a drill pin (3.0 mm drill pin) with a slotted open eyelet, and in accordance with a third embodiment of the present invention;

FIG. 6(b) illustrates a left side view of the drill pin of FIG. 6(a);

FIG. 6(c) illustrates a bottom view of the drill pin of FIG. 6(a);

FIG. 6(d) illustrates a right side view of the drill pin of FIG. 6(c);

FIG. 6(e) illustrates an enlarged view of detail A of the drill pin of FIG. 6(a);

FIG. 6(f) illustrates an enlarged view of detail B of the drill pin of FIG. 6(c);

FIG. 6(g) illustrates an enlarged view of detail C of the drill pin of FIG. 6(a);

FIG. 6(h) illustrates a cross-sectional view of the slot (detail C) of the drill pin of FIG. 6(g), taken along line D-D of FIG. 6(g);

FIG. 7(a) illustrates a front view of a drill pin (3.5 mm drill pin) with a slotted open eyelet, and in accordance with a fourth embodiment of the present invention;

FIG. 7(b) illustrates a left side view of the drill pin of FIG. 7(a);

FIG. 7(c) illustrates a bottom view of the drill pin of FIG. 7(a);

FIG. 7(d) illustrates a right side view of the drill pin of FIG. 7(c);

FIG. 7(e) illustrates an enlarged view of detail A of the drill pin of FIG. 7(a);

FIG. 7(f) illustrates an enlarged view of detail B of the drill pin of FIG. 7(c);

FIG. 7(g) illustrates an enlarged view of detail C of the drill pin of FIG. 7(a);

FIG. 7(h) illustrates a cross-sectional view of the slot (detail C) of the drill pin of FIG. 7(g), taken along line D-D of FIG. 7(g)

DETAILED DESCRIPTION OF THE PREFERRED EMBODIMENTS

Figure 1:
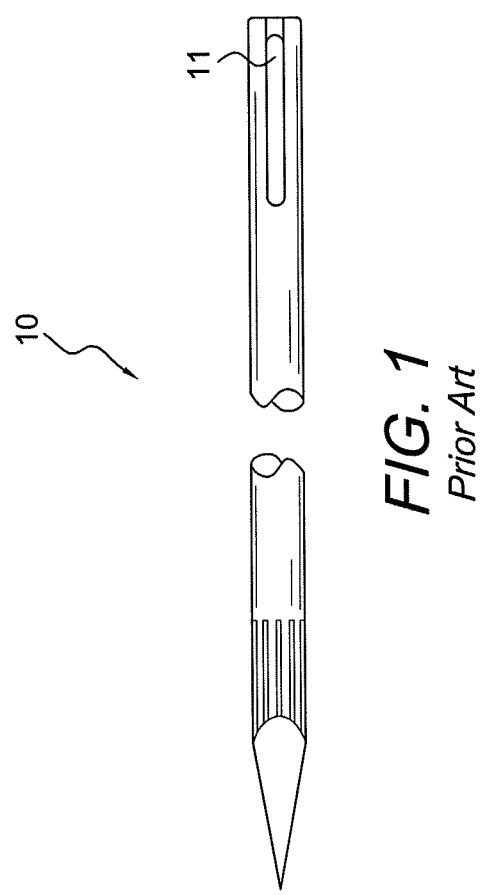
FIG. 1 illustrates a suture pin with a suture eyelet as known in the prior art.

The present invention provides instruments and methods for ligament reconstruction, involving suture and/or graft passage, employing a suture passing mechanism (a securing mechanism) attached to a pin. The suture passing mechanism may include a loop (for example, a wire loop or suture loop) securely attached to a pin (for example, a drill pin). The loop may be crimped onto the pin, or welded on the end of the drill pin (in place of the eyelet formed within the pin), to alleviate the difficulty in threading the eyelet and to lower the manufacturing cost of the pin.

Alternatively, the suture passing mechanism may include a slotted suture eyelet (i.e., a longitudinal slot) provided at a proximal end of a pin and within the shaft of the instrument, to allow suture loading from the side of the instrument. In this manner, loading of the sutures on the pin becomes less difficult and the overall procedure is less time consuming.

Referring now to the drawings, where like elements are designated by like reference numerals, FIGS. 2 to 7(a)-(h) illustrate suture passing constructs 100, 200, 300, 400 formed according to methods of the present invention. As detailed below, suture passing constructs 100, 200, 300, 400 are provided with suture passing mechanisms 120, 220, 320, 420 that allow passing and/or threading of at least one flexible strand (such as suture strand, suture chain formed of suture loops formed and connected by suture, suture tape and/or FiberWire® suture, among others) through tissue or around tissue. The at least one flexible strand may be attached to anatomical tissue (for example, a graft used for ligament reconstruction) or to an additional flexible strand (such as a strand used in connection with a suture anchor/button construct).

Figure 2:
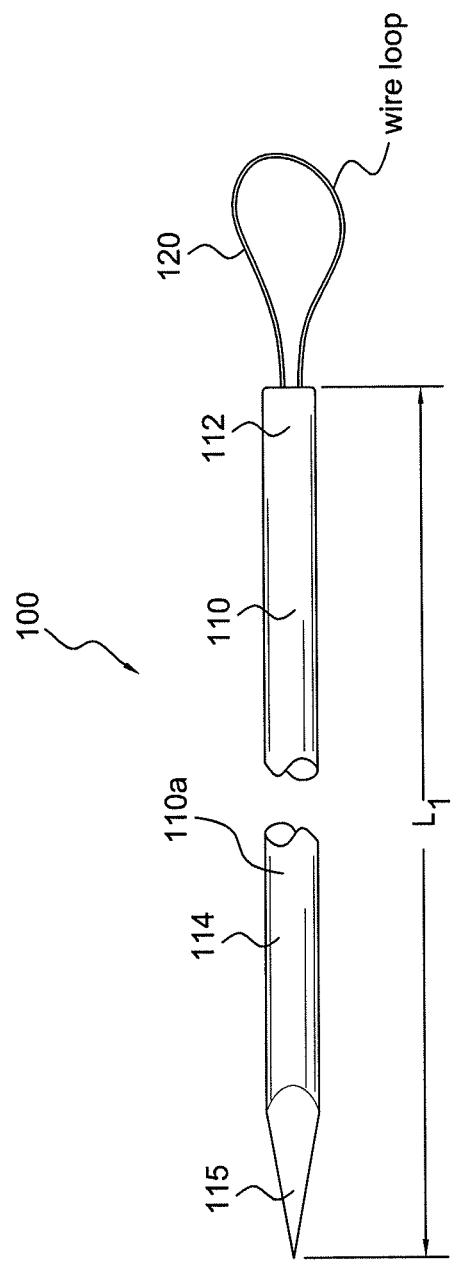
FIG. 2 illustrates a suture pin with a wire loop for suture passing, and in accordance with a first embodiment of the present invention.
Figure 3:
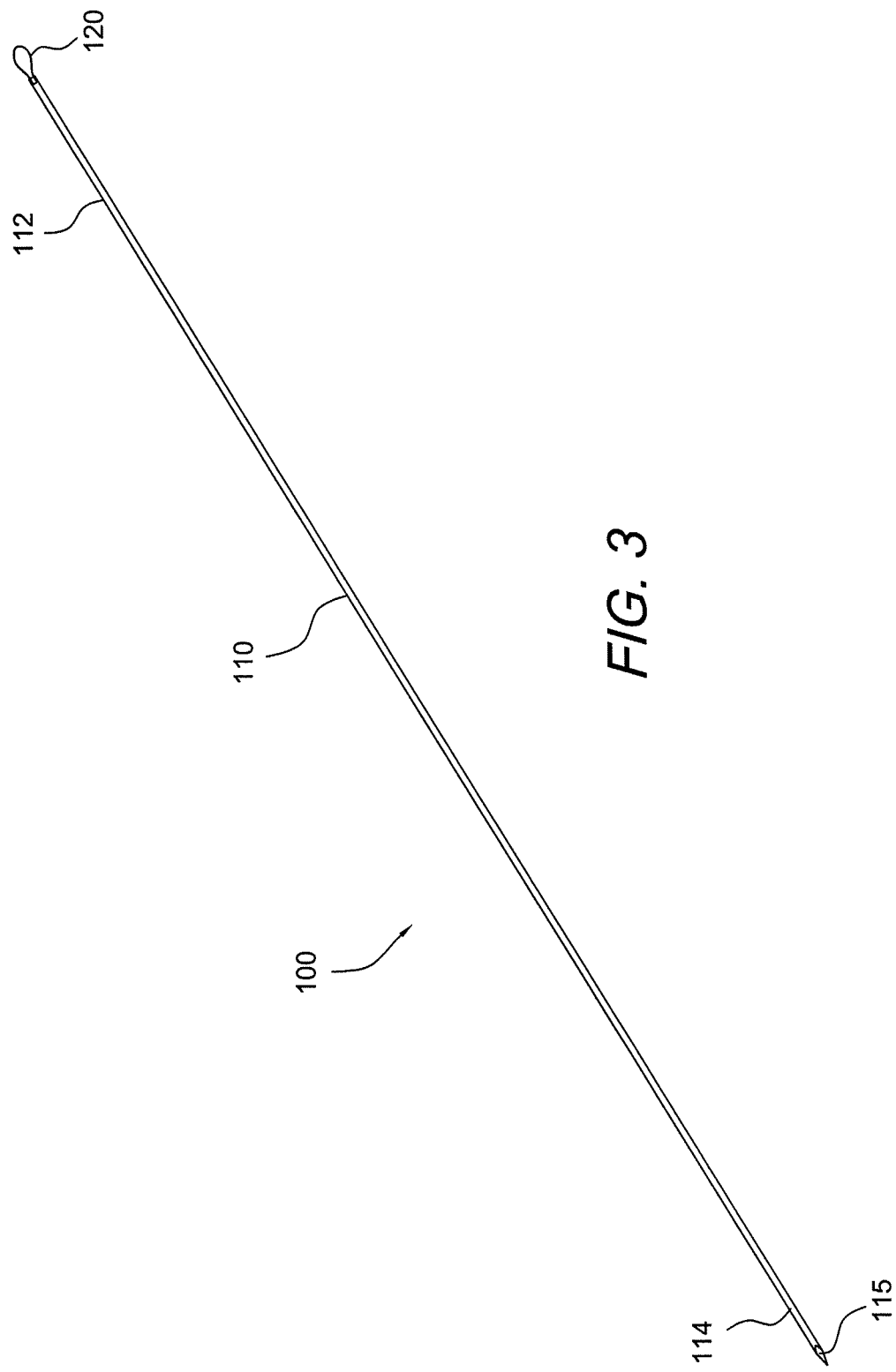
FIG. 3 illustrates a perspective view of the suture pin with wire loop of FIG. 2.
Figure 4:
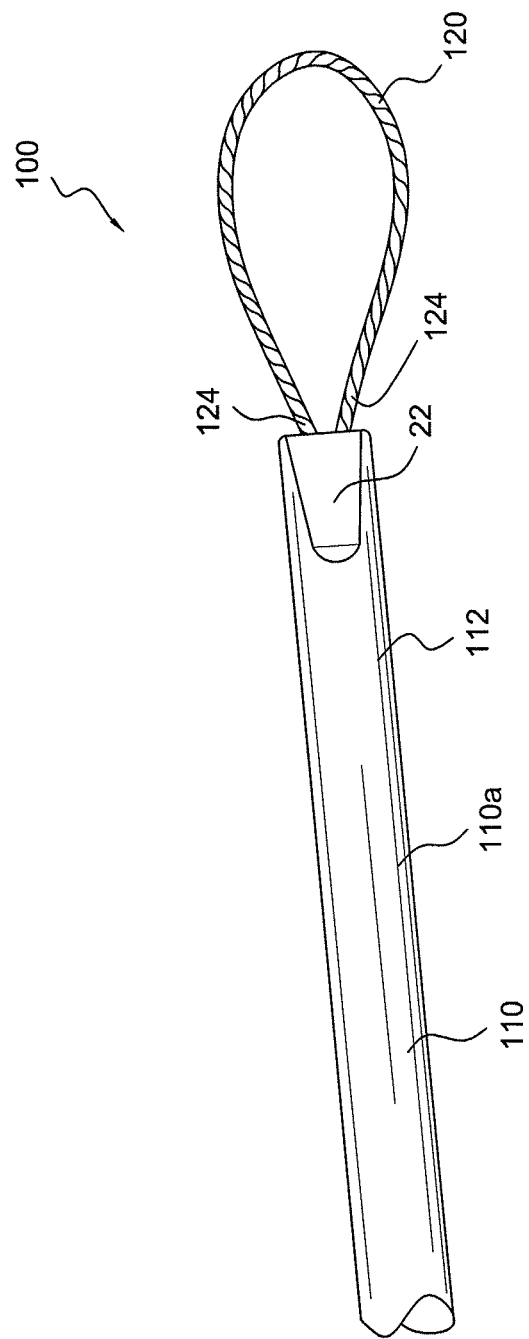
FIG. 4 illustrates an enlarged view of the proximal end of the suture pin with wire loop of FIG. 3.

In a first exemplary embodiment, and as illustrated in FIGS. 2-4, suture passing construct 100 of the present invention comprises a pin 110 with a loop 120 attached thereto. The pin 110 may be, for example, a drill pin, a guide pin or a beath pin, among others. The pin 110 comprises shaft 110a which may be formed of metals, preferably nitinol or stainless steel, metal alloys, or combination of metals and/or metal alloys. Additional details of the pin 110 and loop 120 are illustrated in FIGS. 3 and 4.

The loop 120 may be a suture loop 120 or a wire loop 120 that is attached to proximal end 112 of the pin 110. The loop 120 may be crimped onto the shaft 110a of pin 110, or welded on the end of the drill pin 110 (in place of the conventional eyelet formed within the pin).

The loop 120 of the present invention may be formed of any flexible material. In the preferred embodiment, the loop is formed of a high strength suture material such as Arthrex FiberWire® suture, which is described in U.S. Pat. No. 6,716,234 to Grafton et al., the disclosure of which is incorporated by reference in its entirety. FiberWire® suture is formed of an advanced, high-strength fiber material, namely ultrahigh molecular weight polyethylene (UHMWPE), braided with at least one other fiber, natural or synthetic, to form lengths of suture material.

Loop 120 may be attached directly or indirectly to the shaft 110a of pin 110 (i.e., the loop may be formed integral to the pin 110 (during manufacturing) or attached to the shaft 110a of pin 110 after the formation of the pin). Loop 120 may have various shapes and may be formed of various materials (for example, nitinol or suture, preferably a high strength suture material) and may have various dimensions. In an exemplary embodiment only, and as shown in FIG. 4, the wire loop 120 may be a 3-strand braided nitinol wire that is connected to, and extends away from, the shaft 110a of the pin 110.

Loop 120 of the pin 110 may be securely fitted within cutout section 22 of the shaft 110a of pin 110 (as shown in detail in FIG. 4, for example). Loop 120 may be attached to cutout section 22 of the proximal shaft region 112 by various methods known in the art such as crimping, for example.

Preferably, the diameter of the wire 120 is of about 0.25 to about 1.0 mm, more preferably of about 0.5 mm, so that when the ends 124 of the wire are brought together to form the loop, the combined end region has a diameter about equal to, or smaller than, the diameter of the cutout section 22 of the pin 110, to allow secure engagement of the loop to the pin 110.

In an exemplary embodiment, and as illustrated in FIGS. 2-4, distal region or distal end 114 of the pin 110 terminates in a sharp tip (drill tip) 115 which may also be formed of a material similar to, or different from, the material of the shaft of pin 110. Preferably, both the shaft and drill tip 115 are formed of stainless steel. In an exemplary embodiment, the length L1 (FIG. 2) of the drill pin 110 is about 180-200 mm, more preferably of about 190 mm.

FIGS. 5(a)-(e), 6(a)-(h) and 7(a)-(h) illustrate additional embodiments of the present invention, according to which suture passing constructs 200, 300, 400 include pins 210, 310, 410 provided with slotted suture eyelets 220, 320, 420 at their most proximal ends 212, 312, 412. FIGS. 5(a)-(e) illustrate an exemplary 2.4 mm suture pin with a sharp tip at distal end 211 terminating in a sharp end 215. In the exemplary embodiment shown in FIGS. 5(a)-(e), sharp end 215 is a 3-sided trocar (3-facet trocar with about 10 degree grind angle flat to centerline) with over knurl 216. As in the previously-described embodiment, the sharp tip (drill tip) 215 may be formed of a material similar to, or different from, the material of shaft 210a of the pin 210. In an exemplary embodiment only, the shaft 210a and the sharp tip 215 are formed of stainless steel.

Eyelet 220 is a side open eyelet 220 which, according to an exemplary embodiment, may be a longitudinal slot that allows suture loading from the side of the instrument. In this manner, loading of the sutures on the pin 210 becomes less difficult and the overall procedure is less time consuming.

Slotted suture eyelet 220 shown in FIG. 5(a) may comprise an oblong or transversal cutout section 221 which is in direct communication with a longitudinal cutout section 222. The transversal cutout section 221 allows easy passage and loading of a suture from a lateral side of the pin. Longitudinal section 222 is about parallel to longitudinal axis 280 of the shaft 210a of the pin 210. In an exemplary embodiment, the length L2 (FIG. 5(e)) of the drill pin 210 is about 160-200 mm, more preferably of about 170 mm.

FIGS. 6(a)-(h) and 7(a)-(h) illustrate suture passing constructs 300, 400 which are similar to the suture passing construct 200 of FIGS. 5(a)-(e) in that suture passing constructs 300, 400 also include pins 310, 410 provided with a slotted suture eyelet 320, 420 (at their most proximal ends 312, 412) which are similar to the slotted suture eyelet 220 of pin 210 of FIGS. 5(a)-(e). However, pins 310, 410 have cutting tips (drill tips) 315, 415 in the form of a spade, as shown in FIGS. 6(a), 6(c), 6(e) and 6(f), and FIGS. 7(a), 7(c), 7(e) and 7(f), respectively. Suture passing construct 300 is a 3.0 mm drill pin with slotted suture eyelet 320, while suture passing construct 400 is a 3.5 mm drill pin with slotted suture eyelet 420. Suture eyelets 320, 420 are also provided with oblong or transversal cutout section 321, 421 which is in direct communication with a longitudinal cutout section 322, 422. The transversal cutout section 321, 421 allows easy passage and loading of a suture from a lateral side of the drill pin. Longitudinal section 322, 422 is about parallel to longitudinal axis 380, 480 of the shaft 310a, 410a of drill pin 310, 410.

As in the previously-described embodiments, the drill tip 315, 415 may be formed of a material similar to, or different from, the material of shaft 310a, 410a of the pin 310, 410. In an exemplary embodiment only, the shaft 310a, 410a and the sharp tip 315, 415 are formed of stainless steel. Shaft 310a, 410a may be also provided with laser marks 333, 444, as shown in FIGS. 6(*a*) and 6(*d*), and FIGS. 7(*a*) and 7(*d*) (illustrating exemplary graduated laser marks centimeter numbers 1 through 20).

Suture passing constructs 100, 200, 300, 400 of the present invention (comprising a pin with a suture securing and passing mechanism, such as a wire loop or a side slot) may be employed in surgical methods for tissue repair and/or fixation, such as ligament repairs involving threading suture through tissue, or around tissue, with maximum suture fixation strength, or methods of securing tissue to tissue.

In an exemplary embodiment only, the suture passing construct 100, 200, 300, 400 of the present invention may be employed for fixation of anatomical tissue during surgical applications, for example, for suture and graft passage through a tunnel or socket formed in a bone, for ACL reconstruction. The procedure involves drilling of a graft tunnel between two bones (for example, femur and tibia) with the suture passing construct 100, 200, 300, 400 of the present invention and simultaneously passing of the suture attached to tissue (graft or ligament or tendon), the suture being attached to the suture passing mechanism 120, 220, 320, 420 of the construct 100, 200, 300, 400 within the graft tunnel.

Figure 8:
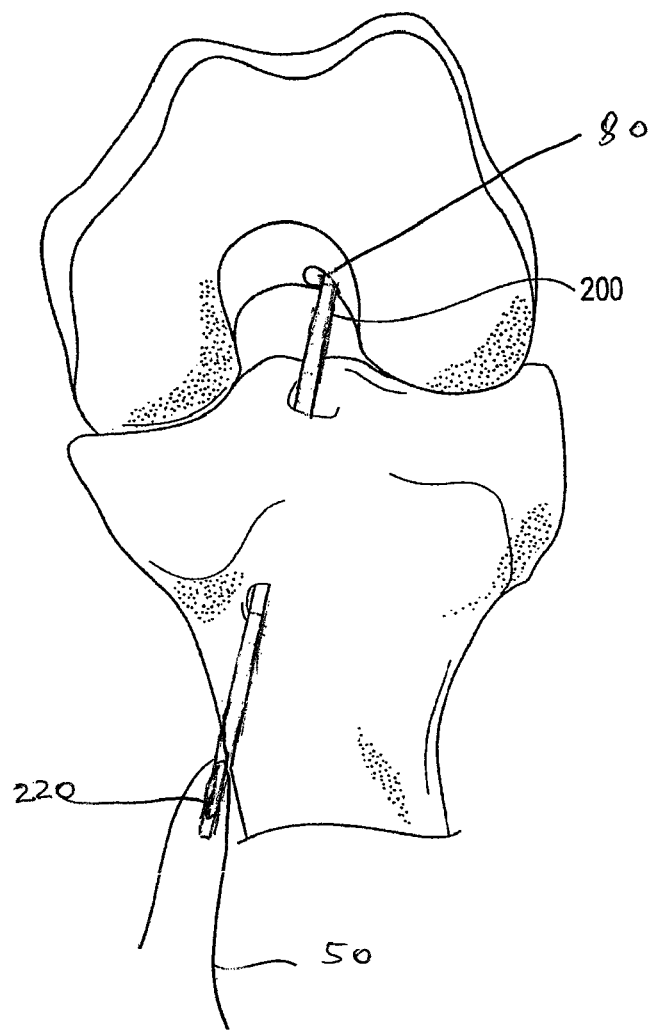
FIG. 8 illustrates a method of ACL reconstruction employing the drill pin of the present invention.

In an exemplary embodiment, as illustrated in FIG. 8, a method of suture passing according to the present invention comprises inter alia the steps of: (i) providing a suture passing construct 100, 200, 300, 400 of the present invention (comprising a pin (such as a drill pin) provided with a suture passing mechanism such as a wire loop 120 or a side slot 220, 320, 420) in the vicinity of a bone; (ii) attaching at least one flexible strand 50 (optionally with attached tissue such as ligament, tendon, or graft) to the suture passing mechanism 220 of the suture passing construct 100, 200, 300, 400; (iii) forming a socket or bone tunnel 80 with the suture passing construct 100, 200, 300, 400 of the present invention; and (iv) simultaneously, passing the at least one flexible strand 50 (attached to the suture passing construct 100, 200, 300, 400) through at least a portion of the bone socket or tunnel 80.

In yet another exemplary embodiment, a method of anatomical tissue repair according to the present invention comprises inter alia the steps of: (i) providing a suture passing construct 100, 200, 300, 400 of the present invention (comprising a pin (such as a drill pin) provided with a suture passing mechanism such as a wire loop 120 or a side slot 220, 320, 420) in the vicinity of a bone; (ii) attaching tissue such as ligament, tendon, or graft, to at least one flexible strand; (iii) attaching the at least one flexible strand (with the attached tissue) to the suture passing mechanism of the suture passing construct 100, 200, 300, 400; (iv) forming a socket or bone tunnel with the suture passing construct 100, 200, 300, 400 of the present invention and, simultaneously, passing the at least one flexible strand and the attached tissue through at least a portion of the bone socket or tunnel; and (v) securing the tissue to the bone socket or tunnel.

In yet another exemplary embodiment, a method of ligament reconstruction according to the present invention comprises inter alia the steps of: (i) providing a suture passing construct 100 of the present invention (comprising a pin (such as a drill pin) provided with a braided nitinol loop 120 in the vicinity of a bone; (ii) attaching a ligament, tendon, or graft to at least one flexible strand; (iii) passing the at least one flexible strand (with the attached ligament, graft or tendon) through the braided nitinol loop 120; (iv) forming a socket or bone tunnel with the suture passing construct 100 of the present invention and, simultaneously, passing the at least one flexible strand and the attached ligament, graft or tendon through at least a portion of the bone socket or tunnel; and (v) securing the ligament, graft or tendon to the bone socket or tunnel.

The suture passing construct 100, 200, 300, 400 of the present invention may be employed for passing a flexible strand (such as suture, suture chain, or FiberWire® suture) or a plurality of flexible strands through any bone tunnels or bone openings (or through tunnels formed in adjacent bones or bone segments). The flexible strand or strands may be attached to tissue such as graft, ligament or tendon.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

The invention claimed is:

1. A method of passing a suture attached to tissue, the method comprising the steps of:
providing an uncannulated suture passing drill pin in the vicinity of a first surface of a bone, the drill pin comprising a shaft having a proximal end, a most distal end terminating in a sharp tip configured to drill a socket or tunnel through bone, the sharp tip having a spade configuration with a diameter greater than any remaining portion of the shaft of the drill pin, and a suture passing mechanism located at the proximal end of the shaft, the suture passing mechanism comprising a wire loop attached to a most proximal end of the shaft or a side longitudinal slot provided within the shaft and at the proximal end of the shaft;
attaching tissue to a flexible strand to form a flexible strand with attached tissue;
subsequently, securing the flexible strand with attached tissue to the suture passing mechanism of the drill pin;
inserting the drill pin with the flexible strand with attached tissue into the bone after securing the flexible strand with attached tissue to the drill pin;
advancing the drill pin with the flexible strand with attached tissue from the first surface of the bone to a second surface of the bone while drilling the bone with the drill pin to form a bone socket or tunnel while simultaneously passing the flexible strand with attached tissue through the bone socket or tunnel, wherein drilling the bone is conducted simultaneously with passing the flexible strand; and
fixating the tissue to the bone socket or tunnel.

2. The method of claim 1, wherein the tissue is a ligament, a graft or a tendon.

* * * * *